United States Patent [19]

Leston

[11] 4,267,392
[45] May 12, 1981

[54] PROCESS FOR OBTAINING PARA-CRESOL AND META-CRESOL FROM A MIXTURE OF METHYLATED AND ETHYLATED PHENOLS CONTAINING META-PARA-CRESOL

[75] Inventor: Gerd Leston, Pittsburgh, Pa.

[73] Assignee: Koppers Company, Inc., Pittsburgh, Pa.

[21] Appl. No.: 53,532

[22] Filed: Jun. 29, 1979

[51] Int. Cl.³ .................... C07C 37/68; C07C 37/74
[52] U.S. Cl. ................................. 568/751; 568/750
[58] Field of Search ................... 568/750, 751, 752

[56] References Cited

U.S. PATENT DOCUMENTS

| 1,980,384 | 11/1934 | Comte | 568/751 |
| 2,366,538 | 1/1945 | Luten et al. | 568/751 |
| 2,835,714 | 5/1958 | Nixon et al. | 568/750 |

FOREIGN PATENT DOCUMENTS 51-98228  8/1976  Japan ........................ 568/751

OTHER PUBLICATIONS

Sharpless, et al., "Journ. Organic Chemistry", vol. 40, No. 9 (1975), pp. 1252–1257.

Primary Examiner—Werren B. Lone
Attorney, Agent, or Firm—J. Timothy Keane; Oscar B. Brumback

[57] ABSTRACT

Para-cresol and meta-cresol are separated from a mixture of methylated and ethylated phenols by a two-stage process wherein the para-cresol is preferentially complexed with one or more anhydrous or dehydrated inorganic salts selected from calcium bromide, lithium bromide, manganese bromide and magnesium chloride. Then the meta-cresol is successively preferentially complexed with calcium bromide from the mixture of methylated and ethylated phenols from which the para-cresol complex has been removed. The anhydrous or dehydrated inorganic salt is added to the mixture of methylated and ethylated phenols including para-cresol and meta-cresol in an amount to give a mole ratio of the salt to para-cresol in the mixture in the range of about 0.5 to one to about 1.5 to one. The para-cresol-salt complex is removed from the mixture of methylated and ethylated phenols and then decomposed to recover the para-cresol. The mixture of methylated and ethylated phenols including meta-cresol from which the para-cresol has been removed has added to it calcium bromide in an amount to give a mole ratio of calcium bromide to meta-cresol in the mixture in the range of about 0.5 to one to around 1.0 to one. The addition is performed in the presence of a non-aqueous solvent and at a temperature in the range of −10° C. to about 40° C. The meta-cresol-salt complex is separated from the second mixture of methylated and ethylated phenols and the complex is decomposed to produce a high purity meta-cresol.

15 Claims, 1 Drawing Figure

PROCESS FOR OBTAINING PARA-CRESOL AND META-CRESOL FROM A MIXTURE OF METHYLATED AND ETHYLATED PHENOLS CONTAINING META-PARA-CRESOL

CROSS-REFERENCE TO RELATED APPLICATIONS

This application is related to applications entitled "Process for Separating Para-Cresol from a Mixture of Methylated and Ethylated Phenols," Ser. No. 53,438, "Process for Obtaining Para-Cresol and Meta-Cresol from a Mixture of Methylated and Ethylated Phenols Characterized by Urea Clathration of Meta-Cresol," Ser. No. 53,531, and "Process for Obtaining Para-Cresol and Meta-Cresol from a Mixture of Methylated and Ethylated Phenols Characterized by Selective Complexation with Calcium Bromide and Sodium Acetate," Ser. No. 53,195, all of Gerd Leston, filed on June 9, 1979, which applications are hereby incorporated by reference.

BACKGROUND OF THE INVENTION

The present invention is directed to a process for separating para-cresol and meta-cresol from a mixture of methylated and ethylated phenols. More particularly, the process of the present invention is directed to obtaining high purity para-cresol from a mixture of methylated and ethylated phenols while also obtaining high purity meta-cresol from a mixture of methylated and ethylated phenols after the para-cresol had been removed.

Mixtures of methylated and ethylated phenolic compounds are derived from coal as products of coal carbonization, or as the middle oil from the hydrogenation of coal, or from the liquefaction of coal, or from petroleum as alkaline extracts of cracked petroleum distillate. Some of the phenolic compounds in the mixture derived from these sources have similar physical properties. These similarities in properties make it difficult to separate some of the phenolic compounds from each other. Para-cresol and meta-cresol are compounds that are usually present in mixtures of methylated and ethylated phenols, and they are difficult to separate from the other methylated and ethylated phenols and from each other. For example, para-cresol is difficult to separate from meta-cresol since both compounds have similar boiling points, namely, 201.8° C. and 202.8° C., respectively. The similarity of boiling points of these two compounds precludes their separation practically by fractional distillation.

There are several known methods for separating para-cresol and meta-cresol isomers from a mixture containing the isomer, such as a commercial mixture having 40–65 percent of meta-cresol, the remainder being para-cresol. These methods include treatment of a mixture containing meta- and para-cresol isomers with complexing agents such as urea, sodium acetate, oxalic acid or the like and separation of the meta- or para-cresol isomers in an adduct form. Other methods include the formation of a solid complex between a reagent and one cresol isomer. The reagents used include ortho-toluidine, oxalic acid and hexamethylenetetramine. Still other methods for separating meta- and para-cresol isomers involve azeotropic distillation with benzyl alcohol, or selective solvent extraction with methanol-ligroin, or hydrolysis of the sulfonic acid of meta- or para-cresol, or dibutylation followed by distillation and debutylation. Another recently suggested method for separating meta-cresol and para-cresol isomers takes advantage of the different melting points of the compounds and involves subjecting the meta- and para-cresol isomer mixture to crystallization at pressures of not less than about 300 atmospheres. Only a few of the foregoing methods of separation have any commercial potentialities, the process usually employed being the butylation method. A more efficient method is thus desired to obtain high purity para-cresol and high purity meta-cresol from mixtures of methylated and ethylated phenols containing compounds such as ortho-ethyl phenol, xylenol and other methylated and ethylated phenols having similar boiling points to para-cresol and meta-cresol.

An article entitled "Rapid Separation of Organic Mixtures by Formation of Metal Complexes", Journal Organic Chemistry, Volume 40, No. 9, 1975, Sharpless, Chong and Scott, describes a convenient and efficient technique for resolving alcohol mixtures. The technique involves preferential complexing of an alcohol by calcium chloride or manganese chloride, examples of useful alcohols being cis- and trans-4-tert-butylcyclohexanol, geraniol and cyclohexanol. The article further notes that other alcohols, such as large and hindered alcohols, form complexes very slowly, and that the speed of complex formation can be increased by using a small amount of a lower aliphatic alcohol as a catalyst for complexing.

SUMMARY OF THE INVENTION

It has been found that para-cresol complexes with certain anhydrous or dehydrated inorganic salts such as calcium bromide, lithium bromide, manganese bromide and magnesium chloride, preferentially over other methylated and ethylated phenolic compounds. It has also been discovered that meta-cresol will complex preferentially with calcium bromide over other methylated and ethylated phenols when the amount of meta-cresol in a mixture of methylated and ethylated phenols is in a molar ratio of at least 2 to 1 over the other methylated and ethylated phenols and is in a molar ratio of at least 15 to 1 over para-cresol, and a low temperature is used during complexing of meta-cresol with calcium bromide. These preferential complexing reactions can be used as a means for separating and purifying para-cresol and meta-cresol from a mixture of methylated and ethylated phenols where such separation is difficult by other means, as, for example, where the methylated and ethylated phenols have similar boiling points to meta-cresol and para-cresol.

The process of the present invention comprises adding to a mixture of methylated and ethylated phenols containing para-cresol and meta-cresol and methylated and ethylated phenols having similar boiling points to para-cresol and meta-cresol one or more anhydrous or dehydrated inorganic salts selected from the group consisting of calcium bromide, lithium bromide, manganese bromide and magnesium chloride, to form a complex predominantly with the para-cresol, whereby the complex may be separated from the mixture and then decomposed to produce predominantly para-cresol, and adding to the mixture of methylated and ethylated phenols from which para-cresol has been removed and which contains predominantly meta-cresol, calcium bromide to yield a meta-cresol-calcium bromide complex, whereby the complex may be separated from the mixture and then decomposed to produce a high purity meta-cresol. In this process, the amount of anhydrous or dehydrated inorganic salt added to the first mixture of methylated and ethylated phenols to produce a para-cresol salt complex is provided in an amount to give a mole ratio of salt to para-cresol in the mixture in the range of about 0.5 to one to 1.5 to one. Preferably, the salt addition is conducted in the presence of a non-aqueous solvent. The addition of calcium bromide to the second mixture of methylated and ethylated phenols from which the para-cresol has been substantially removed is performed with an amount of calcium bromide to give a mole ratio of calcium bromide to meta-cresol in the mixture in the range of about 0.5 to one to about 1.0 to one. Preferably, the calcium bromide addition is also performed in the presence of a non-aqueous solvent and preferably with the mixture having a temperature in the range of about −10° C. to about 40° C.

Another feature of the present invention is the production of the salt-para-cresol complex in the presence of meta-cresol. This complex can be used to initiate complexing with those anhydrous inorganic salts that are slower in forming complexes with the para-cresol. Also, the complex can be used as a chemical intermediate in producing purified para-cresol.

In the process of the present invention, important variables in the first stage include the salt to para-cresol mole ratio, and to a lesser extent, the variables of para-cresol concentration in the mixture of methylated and ethylated phenols, the solvent used and the temperature of complexing. The salt to para-cresol mole ratio is generally in the range of about 0.5 to one to about 1.5 to one. The para-cresol concentration in the mixture of methylated and ethylated phenols can be any concentration, but generally is at least that concentration that can be purified or separated economically. When the amount of para-cresol in the mixture is low, e.g., on the order of 10 weight percent, the preferential complexing of the para-cresol can be enhanced by the use of higher temperatures, e.g., in the order of generally of 70° C. to 130° C. The mixture of methylated and ethylated phenols usually contains, in addition to para-cresol and meta-cresol, other methylated and ethylated phenols having boiling points similar to the para-cresol and meta-cresol. The solvent used must be a non-aqueous solvent, since water will react with the anhydrous inorganic salt to form one or more hydrates. Generally, the non-aqueous solvent should not, itself, complex with the salt or at least not more readily than does the para-cresol. The addition of the salt to the mixture of methylated and ethylated phenols can be initially with or without the use of the solvent, but once the salt is added to the mixture, a solvent should then be employed to facilitate mixing of the salt and the mixture.

Generally, the temperature of complexing ranges from ambient to a temperature of about 130° C., depending upon the concentration of para-cresol in the mixture of methylated and ethylated phenols. If the complex formation is not initiated at higher temperatures then the temperature can be lowered to initiate complex formation, and then raised to the higher temperature. If the para-cresol salt formation is slow, an initiator, such as a lower aliphatic alcohol, or a previously formed complex of the para-cresol and salt, can be used. Once the para-cresol-salt complex is formed, it can be separated from the mixture by any method known to those skilled in the art for separating solid complexes from liquids. Once separated, the para-cresol salt complex can be washed with solvent and then decomposed by thermal decomposition at atmospheric pressure, or by distillation at reduced pressure, or by treatment with water, or by treatment with alcohol. When the complex is decomposed, the high purity para-cresol is recovered and the anhydrous inorganic salt can be recycled for further complex formation with para-cresol, if the decomposition occurred by thermal decomposition or by distillation.

In the second stage of the process of the present invention, where meta-cresol is separated from the mixture of methylated and ethylated phenols from which most of the para-cresol has been removed, important variables are the concentration of the meta-cresol in the mixture, the temperature of complexing and the particular anhydrous or dehydrated salt used. The mixture of methylated and ethylated phenols from which the para-cresol has been removed preferably should contain at least twice as much meta-cresol as other methylated and ethylated phenols. The anhydrous or dehydrated inorganic salt that must be used in complexing the meta-cresol is anhydrous or dehydrated calcium bromide. The temperature of complexing of the meta-cresol and the calcium bromide is a low temperature, generally in the range of −10° C. to 40° C. at atmospheric pressure. The type of solvent and the manner of separation of the complex from the mixture of methylated and ethylated phenols, the manner of decomposing the meta-cresol/calcium bromide complex and the recycling of the calcium bromide are similar to those solvents and methods used in the formation of the para-cresol-salt complex of the first stage. If anhydrous or dehydrated calcium bromide is used to form the complex with para-cresol, the calcium bromide obtained after the decomposition by thermal decomposition or decomposition by distillation, can be recycled to either the complex-forming step for para-cresol or the complex-forming step for meta-cresol.

After the para-cresol-salt complex and meta-cresol-salt complex are separated from the respective mixtures of methylated and ethylated phenols, it is best to dry the complexes and recycle any non-aqueous solvent obtained in the drying process. The non-aqueous solvent can be recycled to the complex-forming step.

DETAILED DESCRIPTION OF THE INVENTION

In the process of the present invention, para-cresol and meta-cresol can be obtained in high purity form from a mixture of methylated and ethylated phenols having similar boiling points to the para-cresol and meta-cresol. Nonlimiting examples of the methylated and ethylated phenolic compounds include ortho-cresol, ortho-ethylphenol, xylenol, and trimethylphenols. It is preferred that the mixture contain substantial quantities of para-cresol and meta-cresol; suitable mixtures include a commercially available mixture of meta-cresol and para-cresol containing from 40–65 percent meta-cresol, the remaining being para-cresol. The other methylated and ethylated phenolic compounds are intended as those methylated and ethylated phenols that do not form complexes with the anhydrous inorganic salts of calcium bromide, lithium bromide, manganese bromide or magnesium chloride, or that are not thermodynamically favored over the para-cresol-salt complex, or that form complexes at a slower rate than para-cresol and meta-cresol.

The process of the present invention is based on a finding that certain anhydrous or dehydrated inorganic salts, when used in a certain mole ratio to para-cresol in the mixture of methylated and ethylated phenols, preferentially form complexes with the para-cresol, and that the remaining mixture of methylated and ethylated phenols containing an amount of meta-cresol that is at least about twice the amount of other methylated and ethylated phenols in the mixture, can preferentially form complexes with calcium bromide at low temperatures. It is believed that formation of the para-cresol-salt complex is thermodynamically controlled, while formation of the meta-cresol-calcium bromide complex is kinetically controlled. The meta-cresol-calcium bromide complex will usually form first, especially in a mixture containing at least two times the amount of meta-cresol to other methylated and ethylated phenols in the mixture; but the para-cresol-salt complex is more thermodynamically stable than the meta-cresol-salt complex, so that given the necessary period of time, formation of the meta-cresol-calcium bromide complex will yield to formation of the para-cresol-salt complex. In order that formation of the meta-cresol-calcium bromide complex is favored, steps may be taken to enhance the kinetically controlled reaction. These steps include having a major amount of meta-cresol in the mixture of methylated and ethylated phenols, i.e., having meta-cresol in an amount at least two times the amount of other methylated and ethylated phenols; or, if meta-cresol is not in excess, then complexation may be conducted at low temperatures, i.e., in a range of $-10°$ C. to $40°$ C. These conditions favor the kinetically controlled formation of the meta-cresol-calcium bromide complex which is then removed from the mixture of methylated and ethylated phenols as soon as possible.

The amount of para-cresol in the mixture of methylated and ethylated phenols and preferably in the mixture of para-cresol and meta-cresol can be practically any amount of para-cresol above about 10 weight percent. The amount of meta-cresol in the mixture of methylated and ethylated phenols, and preferably in the mixture of para-cresol and meta-cresol from which a substantial amount of para-cresol has been removed, should have an amount of meta-cresol in at least a two to one mole excess over other methylated and ethylated phenols in the mixture. An amount of para-cresol in a methylated and ethylated phenolic mixture or a mixture of para-cresol and meta-cresol can be removed fractionally to produce a mixture that contains a two or one molar excess of meta-cresol. Generally, it is preferred that the amount of para-cresol originally present in the mixture of methylated and ethylated phenol be at least about 25 weight percent.

The anhydrous inorganic salts of calcium bromide, lithium bromide, manganese bromide or magnesium chloride that are used in the process of the present invention are the commercial anhydrous salts or dehydrated forms of the salts. Dehydration of the salts can be in any manner known to those skilled in the art. Anhydrous salts are readily prepared from hydrated forms such as aqueous solutions or flaked hydrate forms. It is preferred to heat either the aqueous or flaked form to around 200° C. in air to give the anhydrous material in a solid chunk. The material may be then ball milled or ground for use.

In the first stage of the process of the present invention, a mixture of methylated and ethylated phenols containing para-cresol and meta-cresol is treated to complex the para-cresol by the use of one or more anhydrous inorganic salts (hereinafter referred to as salt). These salts are selected from the group consisting of calcium bromide, lithium bromide, manganese bromide and magnesium chloride. One or more of these salts is added to the mixture in an amount to give a mole ratio of the salt to the para-cresol in the mixture in the general range of about 0.5 to one to about 1.5 to one. If the mole ratio of the salt to para-cresol is about 1.5 to one, other methylated or ethylated phenolic compounds may complex or may complex to an extent which complicates separation of para-cresol from the mixture. If the mole ratio of salt to para-cresol is below about 0.5 to one, then the maximum amount of para-cresol present in the mixture will not be separated and the yield of the process will decrease. The mixture would then have to be treated again with the anhydrous or dehydrated salt in a fractional manner to remove more of the para-cresol in order to obtain a mixture of methylated and ethylated phenols that has the proper amount of meta-cresol so that the meta-cresol can be complexed in the second stage of the process of the present invention. The preferred mole ratio of salt to para-cresol depends on the particular salt used. The preferred mole ratio of the salts are as follows: for calcium bromide, about 0.8 to one to about 1.2 to one; for lithium bromide, about 0.8 to one to about 1.2 to one; for manganese bromide, about 0.8 to one to about 1.2 to one; and for magnesium chloride, about 0.8 to one to about 1.2 to one. These ranges are all based on the mole ratio of salt to para-cresol contained in the mixture. To obtain the mole ratio of salt to para-cresol in the mixture, it is necessary to determine the amount of para-cresol in the mixture of the methylated and ethylated phenolic compounds. This can be done by any analytical technique known to those skilled in the art for determining an amount of para-cresol in a mixture of organic compounds.

The addition of the proper amount of salt can be performed in the presence or absence of a non-aqueous solvent. If the solvent is not present upon the initial addition of the salt to the mixture of methylated and ethylated phenolic compounds, it must be added at a later time when, upon formation of the complex, the mixing of the salt and the mixture becomes difficult. The non-aqueous solvent is added in an amount to facilitate mixing of the components. The non-aqueous solvent should not complex with the salt, but if it does, then it must complex to a lesser extent than the para-cresol. A few examples of non-aqueous solvents that can be used are benzene, toluene, methylene chloride, chlorobenzene, or ortho-dichlorobenzene, and lower aliphatic alicyclic compounds such as hexane, as well as oxygenated compounds like ethers, ketones and esters, provided that any complex that is formed with the solvent is weaker than the complex formed with para-cresol. The preferred non-aqueous solvent is toluene because of its low cost.

During the addition of the components and during complexing of the salt and para-cresol, the temperature of the mixture is in the range of about ambient temperature, generally around 20° C., to about 130° C. at atmospheric pressure. If superatmospheric or subatmospheric pressures are employed, the temperature will vary accordingly. Increases in the temperature moderately within this range during complexing will increase the rate of complex formation. If the complex is not initiated at the higher temperatures within the above range, the temperature can be lowered to initiate complexing and then raised to increase the rate of complexing. The higher temperatures are preferred when there is a small amount, e.g., around 15 weight percent of the para-cresol in the mixture.

If complex formation with a particular salt is not initiated within a reasonable time, an initiator may be used to catalyze complex formation. Such initiators include normal aliphatic alcohols such as anhydrous ethanol, anhydrous propanol and anhydrous butanol. A catalytically effective amount of initiator to be used would be around 1 to about 10 weight percent. Alternatively, a useful initiator is a previously formed complex of para-cresol and calcium bromide, lithium bromide, manganese bromide, or magnesium chloride. A catalytically effective amount of the complex used may be in the range of about 1 to about 10 weight percent of the mixture being treated. It is preferred that anhydrous ethanol be used as the complex initiator or, alternatively, that the complex containing the same salt be used as a complex initiator.

The time taken for the complex formation varies for the particular salt used. Lithium bromide is extremely fast in forming the complex with the para-cresol while calcium bromide, magnesium chloride and manganese bromide are somewhat slower. Lithium bromide forms a complex within around about three to five minutes compared with several hours for the other salts. The preferred anhydrous inorganic salt that is used in the first stage of the present invention is calcium bromide since it has high selectivity and gives good conversions and since calcium bromide must be used in the second stage of the present process.

Once the para-cresol-salt complex, preferably the para-cresol-calcium bromide complex, is formed, the complex is separated from the mixture of methylated and ethylated phenols, preferably a mixture of para-cresol and meta-cresol. This separation can be by any method and in any equipment known to those skilled in the art for separation of a solid complex from a liquid solution. Preferably, the complex is separated by filtration to render a supernatant liquid containing the methylated and ethylated phenols, preferably meta-cresol, in a proper mole ratio of two to one of meta-cresol to other methylated and ethylated phenols. The filtered-out para-cresol-salt complex is decomposed to release the para-cresol so that the salt can be recycled for additional complexing.

In the second stage of the process of the present invention, the supernatant liquid from the first stage, containing methylated and ethylated phenols and meta-cresol in a proper ratio of two to one meta-cresol to other methylated and ethylated phenols, is treated with calcium bromide to complex the meta-cresol contained therein. If the supernatant liquid does not contain at least a two to one ratio of meta-cresol to other methylated and ethylated phenols, the supernatant can be treated again to remove additional amounts of para-cresol, in accordance with the procedures of the first stage as discussed above, to achieve a ratio of meta-cresol to para-cresol of at least 9 to 1. To complex the meta-cresol, the mole ratio of meta-cresol to other methylated and ethylated phenols including any remaining para-cresol must be two to one or greater. The calcium bromide is added to this mixture in an amount in a mole ratio range of about 0.5 to one to around 1.0 to one of calcium bromide to meta-cresol in the mixture. The addition and the complexing take place at a low temperature, i.e., in the range of about −10° C. to 40° C. This low temperature favors complexing of meta-cresol with calcium bromide. If the temperature is higher than this range, complexing of the meta-cresol will be less favored; if a temperature lower than the indicated range is used, an insufficient amount of meta-cresol will be complexed to make the process economically feasible.

Once the meta-cresol-calcium bromide complex is formed, the complex is separated from the mixture of methylated and ethylated phenols. This separation can be by any method and in any equipment known to those skilled in the art for separating a solid complex from a liquid solution. Preferably, the complex is separated by filtration to produce a supernatant liquid that contains methylated and ethylated phenols that did not complex and uncomplexed meta-cresol and para-cresol. The meta-cresol-calcium bromide salt complex contains predominantly the meta-cresol, but also may comprise small quantities of para-cresol-salt complex. The filtered meta-cresol-calcium bromide complex is washed with solvent and then decomposed to release the meta-cresol and recover the calcium bromide which can be recycled for additional complexing. The meta-cresol obtained upon decomposition of the complex is a high purity meta-cresol that has a purity in the range of about 97–99 percent.

Before either the para-cresol-salt complex or the meta-cresol-calcium bromide complex is decomposed, it is preferred that the complex be dried to remove the non-aqueous solvent. This drying may be done by any process known to those skilled in the art for drying a solid to remove a solvent. Preferably the drying is performed by vaporizing the solvent at a temperature above the solvent's boiling point but less than the decomposition temperature for the complex. The recovered solvent obtained from the drying step can be recycled to be used in either of the complexing steps.

Decomposition of the para-cresol-salt complex and the meta-cresol-calcium bromide complex is performed separately but in a similar fashion so that the procedures may be discussed together. Decomposition is preferably performed by heating the complexes to the decomposition temperature which is around 200° C. at atmospheric pressure. Alternatively, the complexes can be decomposed by distillation at a reduced pressure, or by hydrolysis, or by cleavage with other agents, such as an alcohol, that forms a stronger complex than the para-cresol or meta-cresol complex. Thermal decomposition is preferred for releasing the para-cresol and meta-cresol and for recovering the salt and calcium bromide since it is the most economic method of decomposition and since the salt recovered can be recycled for use in further complexing. Thermal decomposition can be performed in any equipment known to those skilled in the art to be useful in conducting decomposition reactions. Preferably, the thermal decomposition is performed in a Rinco evaporator at temperatures up to about 200° C. and under reduced pressure. Alternatively, the complexes can be decomposed at a temperature of around 125° C. under reduced pressure conditions. In another alternative embodiment, the complex can be hydrolyzed with sufficient amount of water to decompose all of the complex. Also, since some alcohols form stronger complexes with the salt than the phenolic compounds, the alcohols can be used to cleave the complex. In this cleavage process, the alcohol will be substituted in the complex for the para-cresol or the meta-cresol. The disadvantage of this decomposition method is that the salt is not easily recoverable for recycling. When hydrolysis is used for decomposition, the salt recovered would have to be dehydrated before it could be recycled.

Although the para-cresol recovered from the decomposition reaction is much purer than that of the original mixture of methylated and ethylated phenolic compounds, the purified para-cresol may contain a minor amount of meta-cresol and other methylated and ethylated phenols such as ortho-ethylphenol. If improved purity is desired, the para-cresol can be complexed again and again in a manner similar to fractional distillation. The meta-cresol recovered from the decomposition reaction has a purity in the range of about 98 percent or better, but may contain minor amounts of para-cresol and other methylated and ethylated phenols.

The complex formation of the para-cresol and the anhydrous inorganic salt and the complex formation of the meta-cresol-calcium bromide can be performed in conventional reaction equipment, since the mixture of methylated and ethylated phenolic compounds and the salt are not very corrosive. Also, the complexing can be performed in a batch manner or a continuous manner where the reactants are cascaded from one reaction vessel to another.

DETAILED DESCRIPTION OF THE DRAWING

Figure 1:
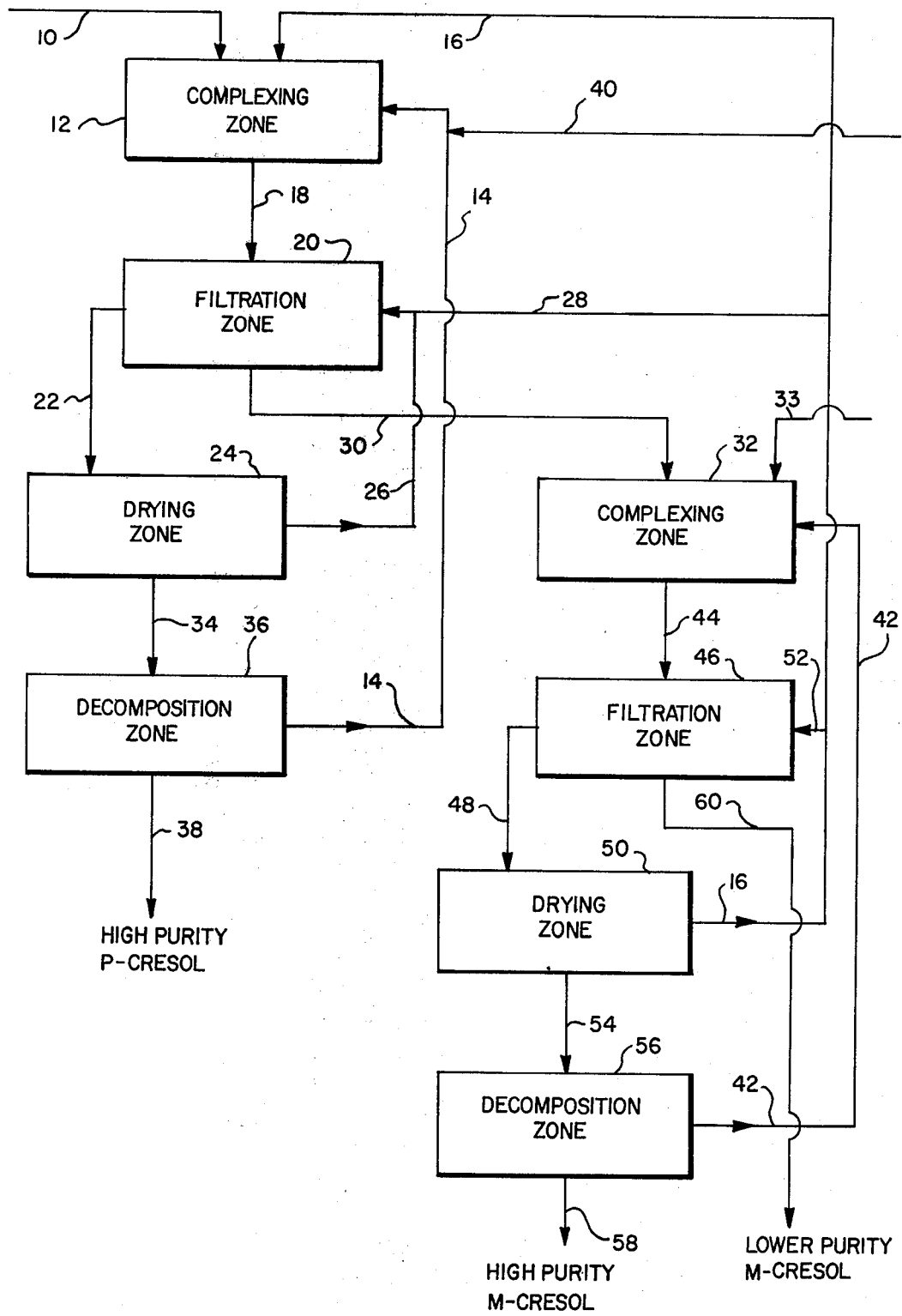
FIG. 1 is a flow diagram of the preferred embodiment of the present invention.

The mixture of methylated and ethylated phenols from which para-cresol and meta-cresol are separated in the preferred embodiment comprises meta-cresol and para-cresol in a two to one mole ratio. This mixture enters a complexing zone 12 through conduit 10. The preferred anhydrous inorganic salt, calcium bromide, enters the complexing zone 12 through conduit 14. The amount of calcium bromide added to complexing zone 12 is preferably an amount which will give a mole ratio of calcium bromide to para-cresol in the range of about 0.7 to one to about 1.0 to one. A non-aqueous solvent, preferably toluene, is added to complexing zone 12 through conduit 16. In complexing zone 12 meta-cresol, para-cresol, toluene and calcium bromide are mixed at a temperature of around 100° C. for about eight hours. During this time, toluene is present in an amount sufficient for complete mixing of the components during the complexing reaction. At the end of the mixing period, a substantial portion of para-cresol forms a complex with calcium bromide. The complex, along with the supernatant liquid containing metal-cresol, and small quantities of ortho-cresol, xylenol, and ortho-ethylphenol, is removed by conduit 18 from complexing zone 12.

The complex and supernatant liquid are conveyed through conduit 18 to a filtration zone 20, where the complex is separated from the supernatant mixture. The wet complex is conveyed from filtration zone 20 through conduit 22 to a drying zone 24, where the complex is dried and the toluene is separated from the complex. The toluene is then recycled through conduit 26 to conduit 28 where it is added with additional toluene and conveyed to filtration zone 20 to wash the wet complex. The supernatant liquid from which the para-cresol-calcium bromide complex has been removed is conveyed from filtration zone 20 through conduit 30 to complexing zone 32.

After the para-cresol-calcium bromide complex has been dried in zone 24, it is conveyed through conduit 34 to decomposition zone 36. In zone 36 the complex is heated to a temperature of around 200° C. at atmospheric pressure to decompose the complex to produce para-cresol and to regenerate the calcium bromide salt. The para-cresol product leaves decomposition zone 36 through conduit 38 and is of a purity of about 98 percent. The regenerated calcium bromide leaves decomposition zone 36 through conduit 14 and is conveyed to complexing zone 12. In an alternative embodiment, additional calcium bromide can be added to conduit 14 through conduit 40 from an outside source.

The supernatant liquid conveyed from filtration zone 20 through conduit 30 and introduced into complexing zone 32 preferably has a mole ratio of meta-cresol to other methylated and ethylated phenols in the mixture of at least two to one. In the preferred embodiment, the supernatant liquid has a concentration of meta-cresol of about 95 percent relative to the total amount of meta- and para-cresol present. In complexing zone 32 the supernatant liquid and calcium bromide delivered through conduit 33 are mixed at a temperature of around 100° C. for about 24 hours. Under these conditions, the meta-cresol in the supernatant liquid preferentially complexes with calcium bromide. The meta-cresol-calcium bromide complex and the uncomplexed mixture is conveyed from zone 32 through conduit 44 to filtration zone 46.

In filtration zone 46 the meta-cresol-calcium bromide complex is separated from the uncomplexed mixture. The complex is withdrawn from filtration zone 46 through conduit 48 into drying zone 50 where the complex is dried. Toluene is removed from drying zone 50 through conduit 16. A portion of the toluene is returned to filtration zone 46 through conduit 52 to wash the wet meta-cresol-calcium bromide complex, while the remainder of the toluene continues in conduit 16 to complexing zone 12 for reuse in complexing para-cresol. The dried metal-cresol-calcium bromide complex is conveyed from drying zone 50 through conduit 54 to decomposition zone 56 wherein the complex is decomposed by heating the complex to its decomposition temperature of around 200° C. Under these conditions, the complex is decomposed and meta-cresol is produced along with the regenerated calcium bromide salt. The meta-cresol product, withdrawn from decomposition zone 56 through conduit 58, has a purity of around 98 percent. The regenerated calcium bromide is withdrawn from zone 56 through conduit 42 and is conveyed to complexing zone 32 for further complexing of the meta-cresol.

The uncomplexed mixture leaving filtration zone 46 through conduit 60 consists of 85-95 percent pure meta-cresol. This mixture can be used as a less pure meta-cresol product or can be treated in other ways to obtain pure meta-cresol.

The following examples set forth specific embodiments of the invention. However, the invention is not to be construed as being limited to these embodiments for there are, of course, numerous possible variations and modifications. All parts and percentages recited in the examples and throughout the specification are by weight, unless otherwise specified.

EXAMPLE I

A reaction vessel equipped with heating and stirring means, a drying tube and a thermometer is charged with 216 parts of a mixture comprising about 65 weight percent meta-cresol and about 35 weight percent para-cresol, 870 parts toluene and 160 parts of para-cresol-activated calcium bromide. The material, "para-cresol-activated calcium bromide," is calcium bromide salt which is reclaimed from decomposed para-cresol-calcium bromide complex. The components are heated to 100° C. with mixing and about 430 parts toluene are then added to the mixture. Mixing of the components is continued for about 8.5 hours, after which time the mixture is allowed to cool. The solid complex is filtered from the mixture and then washed with about 130 parts toluene. Water in excess is added to hydrolyze the solid complex into para-cresol and calcium bromide. Data from gas chromatographic analysis of the product and the supernatant liquid are reported in Table I.

To the filtrate comprising the supernatant liquid is added 205 parts meta-cresol-activated calcium bromide. The material, "meta-cresol-activated calcium bromide," is calcium bromide salt which is reclaimed from decomposed meta-cresol-calcium bromide complex. The mixture is vigorously stirred with the temperature being maintained in a range of 0° C. to −5° C. After 40 minutes the mixture is seeded with a catalytic amount of meta-cresol-calcium bromide complex. Mixing continues for a total of seven hours during which time gas chromatographic analyses of samples of the complex and the supernatant liquid are made as listed in Table I. Mixing is discontinued for about 16 hours during which time the temperature of the reaction mixture is maintained in the range of 0° C. to −5° C. Mixing then continues for 15 more hours with samples being taken bromide. The filtrate is then cooled to a temperature in the range of 0° C. to −5° C. To the cooled filtrate is added 180 parts of meta-cresol-activated calcium bromide. The mixture is then stirred for 7.5 hours with the temperature being maintained at 0° C. to −5° C. The filtrate is subsequently subjected to mixing cycles as generally set forth in Example I. Data from gas chromatographic analysis of samples of the hydrolyzed complexes and supernatant solutions are listed in Table II.

TABLE I

| Time/Temp. | Sample | G. C. Analyses, Relative % | | | |
|---|---|---|---|---|---|
| | | p-cresol | m-cresol | o-cresol | 2,6-xylenol |
| Initial | | ca.35 | ca.65 | | |
| 8.5 hrs/100° C. | Hydrolyzate | 98 | 2 | | |
| | | 97 | 3 | | |
| | Supernatant | 96.8 | 3.2 | | |
| 3 hrs/0 to −5° C. | Hydrolyzate | 1 | 99 | | |
| | Supernatant | 3.8 | 96.2 | | |
| 7 hrs/0 to −15 | Hydrolyzate | 0.6 | 99.4 | | |
| | Supernatant | 5.5 | 94.5 | | |
| 15 hrs/0 to −5° C. | Hydrolyzate | 1.18 | 98.8 | | |
| | Supernatant | 5.84 | 92.3 | 0.62 | 1.24 |
| 21.5 hrs/0 to −5° C. | Hydrolyzate | 1.17 | 98.8 | | |
| | | 1.61 | 98.4 | | |
| | Supernatant | 4.08 | 94.5 | 0.23 | 1.13 |
| | | 5.63 | 92.1 | 0.75 | 1.56 |
| 28 hrs/0 to −5° C. | Hydrolyzate | 1.16 | 98.8 | | |
| | | 1.25 | 98.8 | | |
| | Supernatant | 4.70 | 93.8 | 0.28 | 1.24 |

TABLE II

| Time/Temp | Sample | G. C. Analyses, Relative % | | | |
|---|---|---|---|---|---|
| | | p-cresol + 2,4-2,5-xylenol | m-cresol | o-ethylphenol + o-cresol | 2,6-xylenol |
| Initial | | 28.9 | 65.6 | 4.9 | 0.6 |
| 8.5 hrs/100° C. | Hydrolyzate | 96–97 | 3–4 | — | — |
| | Supernatant | 6.8 | 84.7 | 7.4 | 1.1 |
| 7.5 hrs/0 to −5° C. | Hydrolyzate | 2.9 | 97.1 | — | — |
| | | 2.8 | 97.2 | — | — |
| | Supernatant | 7.7 | 77.4 | 12.3 | 2.6 |
| 15 hrs/0° to −5° C. | Hydrolyzate | 2.5 | 97.2 | 0.28 | — |
| | | 3.0 | 96.7 | 0.27 | — |
| | Supernatant | 8.6 | 72.8 | 15.9 | 2.6 |
| 22.5 hrs/0 to −5° C. | Hydrolyzate | 3.3 | 96.6 | 0.14 | — |
| | | 3.3 | 96.6 | 0.15 | — |
| | Supernatant | 7.5 | 80.2 | 10.4 | 1.9 |
| 30 hrs/0 to −5° C. | Hydrolyzate | 2.8 | 97.1 | 0.10 | — |
| | Supernatant | 9.6 | 71.4 | 16.6 | 2.4 | for analysis. Mixing is again discontinued for about 16 hours, the temperature of the reaction mixture being maintained in the range of 0° C. to −5° C. Mixing is then continued for another 15 hours with samples being taken for analysis.

EXAMPLE II

A reaction vessel equipped as in Example I is charged with 234 parts of a commercially available phenolic mixture ("Productol 88") containing 65.6 percent meta-cresol, 28.9 percent para-cresol and 2,4-2,5-xylenol, 4.9 percent ortho-ethylphenol and ortho-cresol, and 0.6 percent 2,6-xylenol. There is also added to the reaction vessel 128 parts of para-cresol-activated calcium bromide together with 870 parts toluene. The mixture is stirred and heated to a temperature of about 100° C., and then 430 parts more toluene is added. Mixing continues for about 8.5 more hours, after which time the solid product formed is filtered from the mixture and washed with 190 parts toluene. The solid complex is hydrolyzed with water to yield para-cresol and calcium Although specific examples of the instant invention have been set forth hereinabove, it is not intended that the invention be limited solely thereto, but is to include all the variations and modifications falling within the scope of the appended claims.

What is claimed is:

1. A process for successively separating para-cresol and meta-cresol isomers from a mixture of methylated and ethylated phenols, comprising:
   (a) adding to the mixture one or more anhydrous or dehydrated inorganic salts selected from the group consisting of calcium bromide, lithium bromide, manganese bromide and magnesium chloride, in an amount to give a mole ratio of said salt to para-cresol in the mixture in a range from about 0.5 to one to about 1.5 to one, in the presence of a non-aqueous solvent to produce a solid complex between predominantly para-cresol and said salt, the mixture having a temperature in a range from about 20° C. to about 130° C. during the salt adding step, said non-aqueous solvent being an organic solvent selected such that any complex formed with said solvent is weaker than the complex formed between para-cresol and said salt;

whereby said complex may be separated from the mixture and then decomposed to produce predominantly para-cresol; and (b) adding to the mixture from which para-cresol has been removed an amount of calcium bromide to give a mole ratio of calcium bromide to meta-cresol in the mixture in a range from about 0.5 to one to about 1.0 to one in the presence of a non-aqueous solvent and at a temperature in a range from about $-10°$ C. to about $40°$ C. to form predominantly meta-cresol-calcium bromide complex, said non-aqueous solvent selected such that any complex formed with said solvent is weaker than the complex formed between meta-cresol and said calcium bromide;

whereby said meta-cresol-calcium bromide complex may be separated from the mixture, and then decomposed to produce predominantly high purity meta-cresol.

2. The process of claim 1 wherein the mixture further includes one or more phenolic compounds selected from the group consisting of ortho-ethylphenol, 2,4-xylenol, 2,5-xylenol, 2,6-xylenol, ortho-cresol and trimethylphenols.

3. The process of claim 1 wherein the mixture from which para-cresol has been removed is a meta-cresol rich mixture having at least a two to one mole ratio of meta-cresol to other methylated and ethylated phenols in the mixture.

4. The process of claim 1 wherein the solvent is toluene.

5. The process of claim 1 wherein the anhydrous or dehydrated inorganic salt is para-cresol-activated calcium bromide.

6. The process of claim 1 wherein the calcium bromide added to the mixture from which para-cresol has been removed is meta-cresol-activated.

7. The process of claim 1 further comprising the steps of:

separating said para-cresol salt complex and said meta-cresol calcium bromide salt complex from their respective mixtures; and decomposing said para-cresol salt complex and said meta-cresol calcium bromide salt complex to produce, respectively, para-cresol and meta-cresol.

8. The process of claim 7 wherein the complexes are decomposed by thermal decomposition at atmospheric pressure.

9. The process of claim 7 wherein the complexes are decomposed by hydrolysis with water or alcohol.

10. The process of claim 7 wherein the complexes are decomposed by cleavage with a lower aliphatic alcohol selected from the group consisting of ethanol, propanol, isopropanol and butanol.

11. The process of claim 7 wherein the para-cresol-containing complex and the meta-cresol-calcium bromide complex separated from their respective mixtures are dried before the complexes are decomposed.

12. The process of claim 11 wherein the non-aqueous solvent obtained from drying is recycled for further complexing reaction.

13. The process of claim 7 wherein the inorganic salt obtained from decomposing the para-cresol salt complex is recycled for further complexing of para-cresol.

14. The process of claim 7 wherein the calcium bromide obtained from decomposition of the meta-cresol-calcium bromide complex is recycled for further complexing of meta-cresol.

15. The process of claim 7 wherein the complexes are decomposed by distillation at reduced pressure.

* * * * *